(12) United States Patent
Hingston et al.

(10) Patent No.: US 10,610,348 B2
(45) Date of Patent: Apr. 7, 2020

(54) MEDICAL DEVICES AND METHODS TO PREVENT BILE REFLUX AFTER BARIATRIC PROCEDURES

(71) Applicant: BOSTON SCIENTIFIC SCIMED, INC., Maple Grove, MN (US)

(72) Inventors: John A. Hingston, Framingham, MA (US); Claude O. Clerc, Marlborough, MA (US); Jonathan Root, Groveland, MA (US); Vishal Shah, Whitehall, PA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 3 days.

(21) Appl. No.: 16/006,033

(22) Filed: Jun. 12, 2018

(65) Prior Publication Data

US 2018/0289462 A1    Oct. 11, 2018

Related U.S. Application Data

(63) Continuation of application No. 15/407,896, filed on Jan. 17, 2017, now Pat. No. 10,016,268, which is a
(Continued)

(51) Int. Cl.
*A61F 5/00* (2006.01)
*A61F 2/04* (2013.01)
(Continued)

(52) U.S. Cl.
CPC .................. *A61F 2/04* (2013.01); *A61F 2/82* (2013.01); *A61M 39/24* (2013.01); *A61F 2/07* (2013.01);
(Continued)

(58) Field of Classification Search
CPC .................. A61F 5/0076; A61F 5/0079; A61F 2002/045; A61F 2/04; A61F 5/00;
(Continued)

(56) References Cited

U.S. PATENT DOCUMENTS

| 4,501,264 | A | 2/1985 | Rockey |
| 4,763,653 | A | 8/1988 | Rockey |

(Continued)

FOREIGN PATENT DOCUMENTS

| WO | 2007136468 A2 | 11/2007 |
| WO | 2008030403 A1 | 3/2008 |
| WO | 2011137318 A2 | 11/2011 |

*Primary Examiner* — Alvin J Stewart

(74) *Attorney, Agent, or Firm* — Seager, Tufte & Wickhem, LLP

(57) ABSTRACT

An endoscopic stent for implantation in a patient after sleeve gastrectomy or biliopancreatic diversion with duodenal switch or biliopancreatic diversion with duodenal switch comprising a stent portion, the stent portion comprising a proximal end portion, the proximal end portion defined by a length of about 50 mm to about 200 mm, an enlarged middle portion, a middle portion having an enlarged diameter relative to the proximal end portion and the distal end portion and defined by a length of about 20 mm to about 80 mm, and a distal end portion and a polymeric sleeve portion engaged to and extending distally from the distal end portion of the stent.

19 Claims, 7 Drawing Sheets

Related U.S. Application Data continuation of application No. 14/749,221, filed on Jun. 24, 2015, now Pat. No. 9,579,186.

(60) Provisional application No. 62/017,595, filed on Jun. 26, 2014.

(51) Int. Cl.
  *A61F 2/82* (2013.01)
  *A61M 39/24* (2006.01)
  *A61F 2/07* (2013.01)
  *A61F 2/24* (2006.01)

(52) U.S. Cl.
  CPC ....... *A61F 2/2475* (2013.01); *A61F 2002/041* (2013.01); *A61F 2002/044* (2013.01); *A61F 2002/045* (2013.01); *A61F 2250/0039* (2013.01); *A61M 2039/2433* (2013.01)

(58) Field of Classification Search
  CPC .... A61F 5/0003; A61F 5/0013; A61B 5/6862; A61B 17/12118
  See application file for complete search history.

(56) References Cited

U.S. PATENT DOCUMENTS

| | | | |
|---|---|---|---|
| 5,820,584 A | 10/1998 | Crabb | |
| 6,146,414 A | 11/2000 | Gelman | |
| 6,302,917 B1 | 10/2001 | Dua et al. | |
| 6,790,230 B2 | 9/2004 | Beyersdorf et al. | |
| 7,025,779 B2 | 4/2006 | Elliott | |
| 7,025,791 B2 | 4/2006 | Levine et al. | |
| 7,037,344 B2 | 5/2006 | Kagan et al. | |
| 7,111,627 B2 | 9/2006 | Stack et al. | |
| 7,121,283 B2 | 10/2006 | Stack et al. | |
| 7,152,607 B2 | 12/2006 | Stack et al. | |
| 7,267,694 B2 | 9/2007 | Levine et al. | |
| 7,354,454 B2 | 4/2008 | Stack et al. | |
| 7,513,914 B2 | 4/2009 | Schurr | |
| 7,608,114 B2 | 10/2009 | Levine et al. | |
| 7,611,534 B2 | 11/2009 | Kapadia et al. | |
| 7,695,446 B2 | 4/2010 | Levine et al. | |
| 7,794,447 B2 | 9/2010 | Dann et al. | |
| 7,815,591 B2 | 10/2010 | Levine et al. | |
| 7,833,280 B2 | 11/2010 | Stack et al. | |
| 7,837,669 B2* | 11/2010 | Dann | A61B 17/00234 604/514 |
| 7,846,138 B2 | 12/2010 | Dann et al. | |
| 7,981,162 B2 | 7/2011 | Stack et al. | |
| 8,029,455 B2 | 10/2011 | Stack et al. | |
| 8,070,800 B2 | 12/2011 | Lock et al. | |
| 8,282,598 B2* | 10/2012 | Belhe | A61F 5/0076 604/103 |
| 8,282,678 B2 | 10/2012 | Yachia et al. | |
| 8,454,686 B2 | 6/2013 | Alkhatib | |
| 8,540,768 B2 | 9/2013 | Stacchino et al. | |
| 8,568,488 B2 | 10/2013 | Stack et al. | |
| 8,591,573 B2 | 11/2013 | Barone | |
| 8,702,641 B2* | 4/2014 | Belhe | A61F 5/0076 604/19 |
| 8,702,642 B2 | 4/2014 | Belhe et al. | |
| 8,728,154 B2 | 5/2014 | Alkhatib | |
| 8,747,453 B2 | 6/2014 | Amplatz et al. | |
| 8,784,354 B2* | 7/2014 | Stack | A61F 5/0089 604/8 |
| 8,870,806 B2 | 10/2014 | Levine et al. | |
| 8,956,318 B2* | 2/2015 | Miller | A61F 2/04 604/264 |
| 9,011,365 B2* | 4/2015 | Connor | A61F 5/0076 600/37 |
| 9,044,300 B2 | 6/2015 | Belhe et al. | |
| 9,161,758 B2 | 10/2015 | Figulla et al. | |
| 9,579,186 B2* | 2/2017 | Hingston | A61F 2/04 |
| 10,016,268 B2* | 7/2018 | Hingston | A61F 2/04 |
| 2002/0193871 A1 | 12/2002 | Beyersdorf et al. | |
| 2002/0198587 A1 | 12/2002 | Greenberg et al. | |
| 2003/0125798 A1 | 7/2003 | Martin | |
| 2003/0187500 A1 | 10/2003 | Jansen et al. | |
| 2004/0039452 A1* | 2/2004 | Bessler | A61F 2/07 623/23.65 |
| 2004/0107004 A1 | 6/2004 | Levine et al. | |
| 2004/0138745 A1 | 7/2004 | Macoviak et al. | |
| 2004/0236411 A1 | 11/2004 | Sarac et al. | |
| 2004/0260389 A1 | 12/2004 | Case et al. | |
| 2005/0049718 A1 | 3/2005 | Dann et al. | |
| 2005/0125075 A1 | 6/2005 | Meade et al. | |
| 2005/0177181 A1* | 8/2005 | Kagan | A61B 17/00234 606/151 |
| 2005/0256587 A1* | 11/2005 | Egan | A61F 2/04 623/23.65 |
| 2005/0273060 A1 | 12/2005 | Levy et al. | |
| 2006/0020247 A1 | 1/2006 | Kagan et al. | |
| 2006/0064120 A1* | 3/2006 | Levine | A61F 2/04 606/153 |
| 2006/0085060 A1 | 4/2006 | Campbell | |
| 2006/0136044 A1 | 6/2006 | Osborne et al. | |
| 2007/0010866 A1* | 1/2007 | Dann | A61B 17/00234 623/1.11 |
| 2007/0142907 A1 | 6/2007 | Moaddeb et al. | |
| 2007/0156233 A1 | 7/2007 | Kapadia et al. | |
| 2007/0265709 A1* | 11/2007 | Rajan | A61F 2/04 623/23.64 |
| 2007/0282452 A1 | 12/2007 | Weitzner et al. | |
| 2007/0282453 A1 | 12/2007 | Weitzner et al. | |
| 2007/0293716 A1* | 12/2007 | Baker | A61F 2/04 600/37 |
| 2008/0033574 A1 | 2/2008 | Bessler et al. | |
| 2008/0058887 A1* | 3/2008 | Griffin | A61N 1/36007 607/40 |
| 2008/0091261 A1 | 4/2008 | Long et al. | |
| 2008/0195226 A1 | 8/2008 | Williams et al. | |
| 2008/0221599 A1 | 9/2008 | Starksen | |
| 2008/0228030 A1* | 9/2008 | Godin | A61B 17/0401 600/106 |
| 2008/0228126 A1* | 9/2008 | Bessler | A61F 2/04 604/9 |
| 2008/0275540 A1 | 11/2008 | Wen | |
| 2008/0288055 A1 | 11/2008 | Paul, Jr. | |
| 2009/0012544 A1* | 1/2009 | Thompson | A61B 17/1114 606/156 |
| 2009/0093767 A1* | 4/2009 | Kelleher | A61F 2/04 604/175 |
| 2009/0093839 A1* | 4/2009 | Kelleher | A61F 2/04 606/192 |
| 2009/0216337 A1* | 8/2009 | Egan | A61F 2/04 623/23.64 |
| 2009/0248171 A1* | 10/2009 | Levine | A61B 17/0401 623/23.65 |
| 2010/0030017 A1* | 2/2010 | Baker | A61B 17/00234 600/37 |
| 2010/0049224 A1* | 2/2010 | Vargas | A61F 5/0036 606/153 |
| 2010/0094390 A1 | 4/2010 | Goldmann et al. | |
| 2010/0114305 A1 | 5/2010 | Kang et al. | |
| 2010/0121423 A1 | 5/2010 | Bernhard et al. | |
| 2010/0191167 A1 | 7/2010 | Laufer | |
| 2010/0204781 A1 | 8/2010 | Alkhatib | |
| 2010/0256775 A1* | 10/2010 | Belhe | A61F 5/0076 623/23.65 |
| 2010/0298631 A1 | 11/2010 | Stack et al. | |
| 2011/0040232 A1 | 2/2011 | Magal | |
| 2011/0046719 A1 | 2/2011 | Frid | |
| 2011/0087146 A1* | 4/2011 | Ryan | A61F 2/04 604/8 |
| 2011/0098800 A1 | 4/2011 | Braido et al. | |
| 2011/0106273 A1* | 5/2011 | Belhe | A61F 5/0076 623/23.64 |
| 2011/0160836 A1 | 6/2011 | Behan | |
| 2011/0295286 A1* | 12/2011 | Harris | A61F 5/0076 606/153 |
| 2011/0307070 A1 | 12/2011 | Clerc et al. | |

(56) References Cited

U.S. PATENT DOCUMENTS

| | | |
|---|---|---|
| 2012/0046733 A1 | 2/2012 | von Oepen et al. |
| 2012/0065571 A1 | 3/2012 | Thompson et al. |
| 2012/0078347 A1 | 3/2012 | Braido et al. |
| 2012/0116286 A1 | 5/2012 | Williams et al. |
| 2012/0184893 A1 | 7/2012 | Thompson et al. |
| 2012/0253259 A1 | 10/2012 | Belhe et al. |
| 2013/0289711 A1 | 10/2013 | Liddy et al. |
| 2013/0324902 A1* | 12/2013 | Miller ............... A61F 2/04 604/8 |
| 2013/0324926 A1* | 12/2013 | Nelson .............. A61F 2/04 604/115 |
| 2013/0325103 A1 | 12/2013 | Arai et al. |
| 2013/0331759 A1* | 12/2013 | Neisz .............. A61F 5/0076 604/8 |
| 2014/0142693 A1 | 5/2014 | Krivoruchko et al. |
| 2014/0142694 A1 | 5/2014 | Tabor et al. |
| 2014/0200502 A1* | 7/2014 | Belhe ............. A61K 35/741 604/8 |
| 2014/0213960 A1 | 7/2014 | Belhe et al. |
| 2014/0243965 A1 | 8/2014 | Benson et al. |
| 2014/0249464 A1* | 9/2014 | Godin ............. A61F 5/0076 604/8 |
| 2014/0257461 A1 | 9/2014 | Robinson et al. |
| 2014/0275747 A1* | 9/2014 | Connor ........... A61F 5/0076 600/37 |
| 2014/0276333 A1* | 9/2014 | Neisz .............. A61F 5/0079 604/8 |
| 2014/0276336 A1 | 9/2014 | Sharma |
| 2014/0276338 A1 | 9/2014 | Pattison et al. |
| 2015/0025625 A1 | 1/2015 | Rylski et al. |
| 2015/0039076 A1 | 2/2015 | Park |
| 2015/0088048 A1 | 3/2015 | Vargas |
| 2015/0374484 A1 | 12/2015 | Hingston et al. |
| 2016/0022463 A1* | 1/2016 | Arita ............... A61F 5/0076 604/8 |
| 2016/0081832 A1 | 3/2016 | Hingston et al. |
| 2017/0035594 A1* | 2/2017 | Sigmon, Jr. ........ A61F 2/04 |
| 2017/0348129 A1* | 12/2017 | Hingston ........... A61F 5/0036 |

* cited by examiner

MEDICAL DEVICES AND METHODS TO PREVENT BILE REFLUX AFTER BARIATRIC PROCEDURES

CROSS REFERENCE TO RELATED APPLICATIONS

This application is a continuation of co-pending U.S. application Ser. No. 15/407,896, filed Jan. 17, 2017, which is a continuation of U.S. application Ser. No. 14/749,221, filed Jun. 24, 2015, now U.S. Pat. No. 9,579,186, which claims priority to U.S. Provisional Application No. 62/017,595 filed Jun. 26, 2014, the contents of which are incorporated by reference in their entirety.

BACKGROUND

The present disclosure relates valve devices and methods for the prevention of bile reflux for bariatric stents.

Obesity is a medical condition in which excess body fat has accumulated to the extent that it may have an adverse effect on health, leading to reduced life expectancy and/or increased health problems. Body mass index (BMI), a measurement which compares weight and height, defines people as overweight (pre-obese) when their BMI is between 25 kg/m$^2$ and 30 kg/m$^2$, and obese when it is greater than 30 kg/m$^2$. Obesity is most commonly caused by a combination of excessive dietary calories, lack of physical activity, and genetic susceptibility. On average, obesity reduces life expectancy by six to seven years. Obesity increases the likelihood of various diseases, particularly heart disease, type 2 diabetes, breathing difficulties during sleep, certain types of cancer, and osteoarthritis. Obesity is the second leading preventable cause of death worldwide, with increasing prevalence in adults and children, and authorities view it as one of the most serious public health problems of the 21st century. The WHO estimated in 2005 that at least 400 million adults (9.8%) worldwide were obese. According to a CDC report, 34% of adults and 17% of children in the United States were obese in 2007-2008. Obesity has been estimated to cause up to 365,000 deaths per year in the United States.

Bariatric (or weight loss) surgeries are surgical treatments for treating severe obesity (BMI greater than 40 kg/m$^2$ or BMI greater than 35 kg/m$^2$) with a comorbidity. The most common bariatric surgery is Roux-en-Y Gastric Bypass (RYGBP) (FIG. 1), in which a small gastric pouch and an alimentary limb (Roux limb) are created and anastomosed to one another and to the patient's jejunum, bypassing part of the small intestine. Other bariatric surgeries, as shown in FIG. 2, may involve removal of a portion of the stomach (sleeve gastrectomy or biliopancreatic diversion with duodenal switch or biliopancreatic diversion with duodenal switch). In biliopancreatic diversion with duodenal switch, about 80 percent of the stomach is removed, forming a thin sleeve-like stomach. The valve that releases food to the small intestine remains (pylorus) along with a limited portion of the small intestine that normally connects to the stomach (duodenum). The surgery bypasses the majority of the intestine by connecting the end portion of the intestine to the duodenum near the stomach (biliopancreatic diversion). This weight-loss surgery is effective but has more risks, such as malnutrition and vitamin deficiencies, and requires close monitoring. It is generally used for people who have a body mass index greater than 50 kg/m$^2$. About 150,000 patients undergo bariatric surgery each year. Long-term studies show the procedures cause significant long-term loss of weight, recovery from diabetes, improvement in cardiovascular risk factors, and a reduction in mortality of 23% to 40%.

It is reported that post-operative leaks occur in about 2% to 3% of bariatric surgery cases, but the real number may be higher due to underreporting. For RYGBP, leaks mostly occur along the stapling line of the gastric pouch and at the gastrojejunal anastomosis. However, leaks can also occur along the Z line between the esophagus and the stomach. Leaks are one of the most dreaded complications after bariatric surgery and are associated with increased morbidity and mortality. Leaks can be treated with several modalities, including site drainage with parenteral nutrition and bowel rest, various endoscopic methods (esophageal stents, clips, glue, sutures), and a second bariatric surgery. These treatment modalities all have drawbacks.

Esophageal stents have been successfully used to treat leaks after sleeve gastrectomy or biliopancreatic diversion with duodenal switch. These stents are prone to migration, however, because their shape is not adapted to the modified stomach geometry after sleeve gastrectomy or biliopancreatic diversion with duodenal switch. Two stents are often employed because existing stents are simply too short for a successful treatment.

For sleeve gastrectomy or biliopancreatic diversion with duodenal switch, most of the leaks occur in the upper part (the proximal third) of the sleeve. This occurs because the upper part is less accessible during surgery and more difficult to staple.

In a majority of cases where leakage occurs, there is a stricture in the incisura region of the stomach that creates an increase in pressure in the upper part of the sleeve. FIG. 3 is included as a representation of the stomach geometry prior to sleeve gastrectomy or biliopancreatic diversion with duodenal switch and FIG. 4 is included as a representation of the stomach geometry after sleeve gastrectomy or biliopancreatic diversion with duodenal switch.

SUMMARY

In one aspect, the present disclosure relates to an endoscopic stent for implantation in a patient after sleeve gastrectomy or biliopancreatic diversion with duodenal switch or biliopancreatic diversion with duodenal switch comprising a stent portion, the stent portion comprising a proximal end portion and defined by a length of about 50 mm to about 200 mm, preferably about 120 mm to about 180 mm with a diameter of about 10 mm to about 30 mm, the proximal end portion defined by a length of about 100 mm to about 200 mm, an enlarged middle portion, the enlarged middle portion having an increased diameter of about 5 mm to about 60 mm and having a length of about 20 mm to about 80 mm, preferably about 30 mm to about 60 mm that is greater than the diameter of the proximal end portion and the distal end portion having a length of about 30 mm to about 300 mm, preferably 30 mm to about 100 mm, more preferably about 40 mm to about 80 mm and a diameter of about 5 mm to about 30 mm, and a distal end portion and a polymeric sleeve portion engaged to the distal end portion of the stent portion and extending distally therefrom.

The endoscopic stent may have the distal end portion defined by a length of 0 mm to about 100 mm, and preferably about 50 mm to about 100 mm.

The endoscopic stent may have the proximal end of the proximal end portion comprising a flare, the distal end of the distal end portion comprises a fare, or both.

The endoscopic stent wherein the sleeve portion is defined by a length of about 200 mm to about 350 mm.

The endoscopic stent may have a polymeric sleeve portion that is elastomeric.

The endoscopic stent may have a polymeric sleeve that comprises silicone. The endoscopic stent may be braided, woven or laser cut.

The endoscopic stent may have the stent portion comprising nickel-titanium alloy, cobalt-chromium-nickel alloy, cobalt-chromium alloy, or stainless steel.

The endoscopic stent may have the stent portion comprising a cover.

The endoscopic sleeve portion may have the enlarged central portion of the stent portion uniformly shaped. In another aspect, the present disclosure relates to an endoscopic stent for implantation in a patient after sleeve gastrectomy or biliopancreatic diversion with duodenal switch comprising a stent portion, the stent portion comprising a proximal end portion, the proximal end portion defined by a length of about 100 mm to about 200 mm, an enlarged middle portion, a middle portion having an enlarged diameter with an increase in the diameter of about 5 mm to about 40 mm relative to the proximal end portion and the distal end portion and defined by a length of about 40 mm to about 80 mm, and a distal end portion, the distal end portion defined by a length of about 50 mm to about 100 mm, and wherein at least a portion of the distal end portion of the stent comprises a device that is configured to open and close.

The endoscopic stent may have the proximal end portion, the distal end portion, or both, comprising a flare, the flare comprising an increased diameter of about 2 mm to about 10 mm relative to the proximal end portion and the distal end portion.

The endoscopic stent may have the device being a one-way valve disposed within the distal end portion between the enlarged middle portion and a distal end of the endoscopic stent.

The endoscopic stent may have the one-way valve comprising a single cusp or multiple cusps.

The endoscopic stent may have the one-way valve being tricuspid.

The endoscopic stent may be woven, braided or laser cut.

The endoscopic stent may have the device being an elastomeric band disposed on an outer surface of the distal end portion at a distal end of the enlarged middle portion.

The endoscopic stent may have the distal end portion of the endoscopic stent comprising a continuous wall configuration.

The endoscopic stent may have at least a portion of the distal end portion comprising reduced radial strength.

In another aspect, the present disclosure relates to an endoscopic stent for implantation in a patient after sleeve gastrectomy or biliopancreatic diversion with duodenal switch comprising a stent portion, the stent portion comprising a flared proximal end portion, an enlarged middle portion and a distal end portion, the stent configured so that the flared proximal end portion is in a distal portion of the esophagus and the enlarged middle portion is disposed within a central portion of the stomach and a polymeric sleeve portion engaged to the distal end portion of the stent portion of the stent portion and extending distally therefrom.

The endoscopic stent may have the distal end of the distal end portion flared.

The endoscopic stent may have distal end portion defined by a length of slightly greater than 0 mm to about 100 mm and the polymeric sleeve portion is defined by a length of about 200 mm to about 350 mm.

In another aspect, the present disclosure relates to a method of making an endoscopic stent, the stent comprising a stent portion and a sleeve portion comprising the steps of providing a mandrel defined by a length of about 150 mm to about 700 mm, preferably about 250 mm to about 700 mm, braiding the stent portion on the mandrel, the stent portion comprising a proximal end portion, the proximal end portion defined by a length of about 50 mm to about 200 mm, preferably about 100 mm to about 200 mm, an enlarged middle portion, a middle portion having an enlarged diameter and defined by a length of about 20 mm to about 80 mm, preferably about 40 mm to about 80 mm, and a distal end portion, coating the stent portion to provide a covering and coating a portion of the mandrel extending beyond the stent portion to provide the sleeve portion of the stent, the sleeve portion defined by a length of about 50 mm to about 350 mm, preferably about 100 mm to about 350 mm, and most preferably about 200 mm to about 350 mm, the sleeve is an extension of the stent coating.

DETAILED DESCRIPTION

While embodiments of the present disclosure may take many forms, there are described in detail herein specific embodiments of the present disclosure. This description is an exemplification of the principles of the present disclosure and is not intended to limit the disclosure to the particular embodiments illustrated.

The following detailed description should be read with reference to the drawings in which similar elements in different drawings are numbered the same. The drawings, which are not necessarily to scale, depict illustrative embodiments and are not intended to limit the scope of the disclosure. Those skilled in the art will recognize that the dimensions and materials discussed herein are merely exemplary and are not intended to limit the scope of the present disclosure.

In some embodiments, the present disclosure relates generally to a stent having a bulge or enlarged middle portion where the bulge is designed to adapt to the antrum pouch created during sleeve gastrectomy or biliopancreatic diversion with duodenal switch (SG) surgery. The role of the bulge is to prevent downwards and/or upwards stent migration and close/insulate any leaks that may occur. The present disclosure is discussed in more detail with respect to the figures below.

In some embodiments, the stent includes a sleeve that extends past the distal end of the stent into the duodenum and past the common bile duct to prevent reflux.

Figure 2:
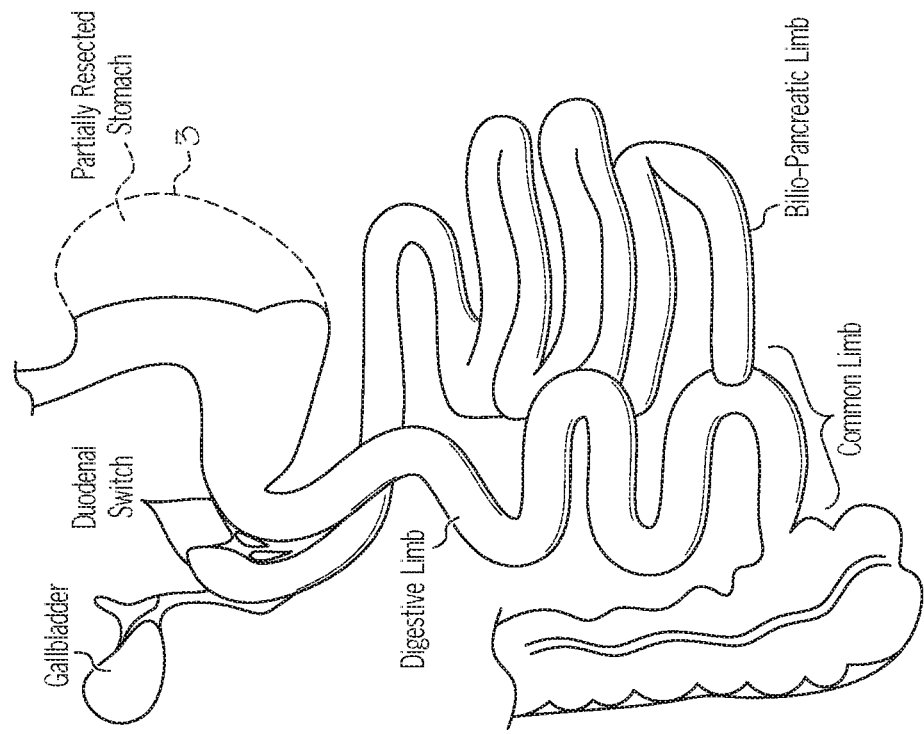
FIG. 2 is a schematic view of portions of an alimentary canal after a biliopancreatic diversion with duodenal switch procedure.
Figure 1:
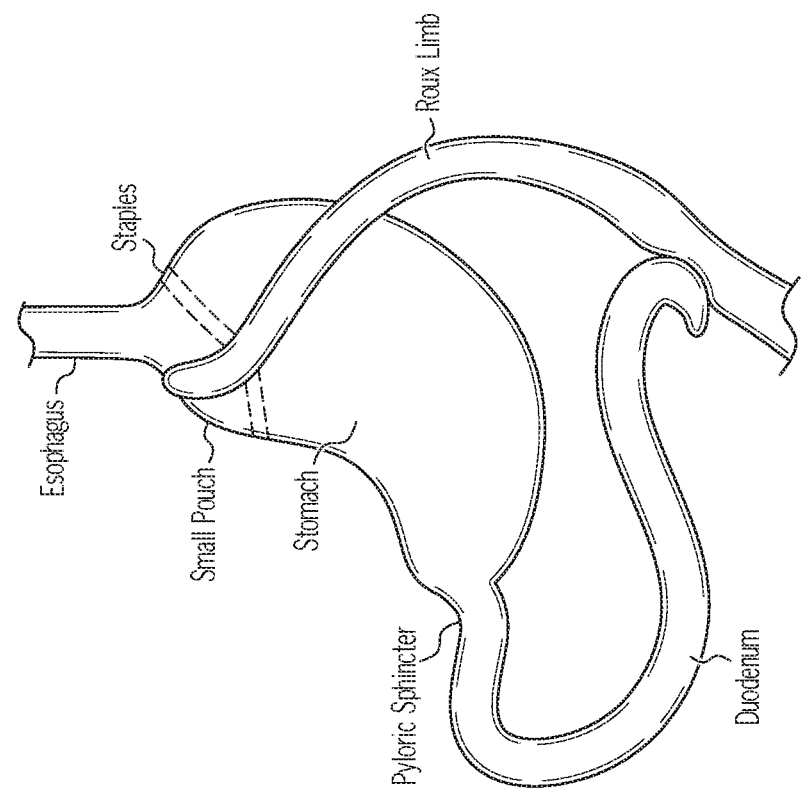
FIG. 1 is a schematic view of portions of an alimentary canal after a Roux-en-Y procedure.
Figure 4:
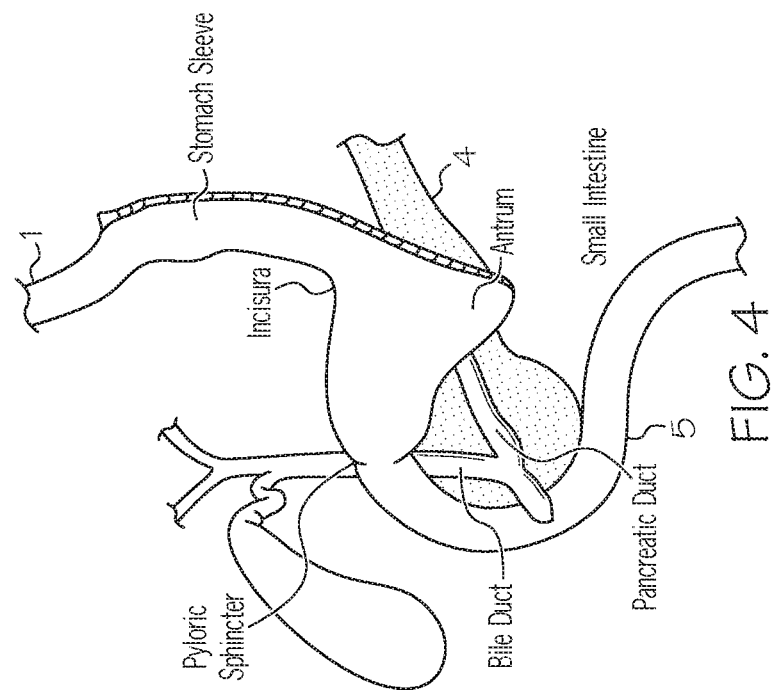
FIG. 4 is a schematic view of the modified geometry of the stomach after sleeve gastrectomy or biliopancreatic diversion with duodenal switch.
Figure 3:
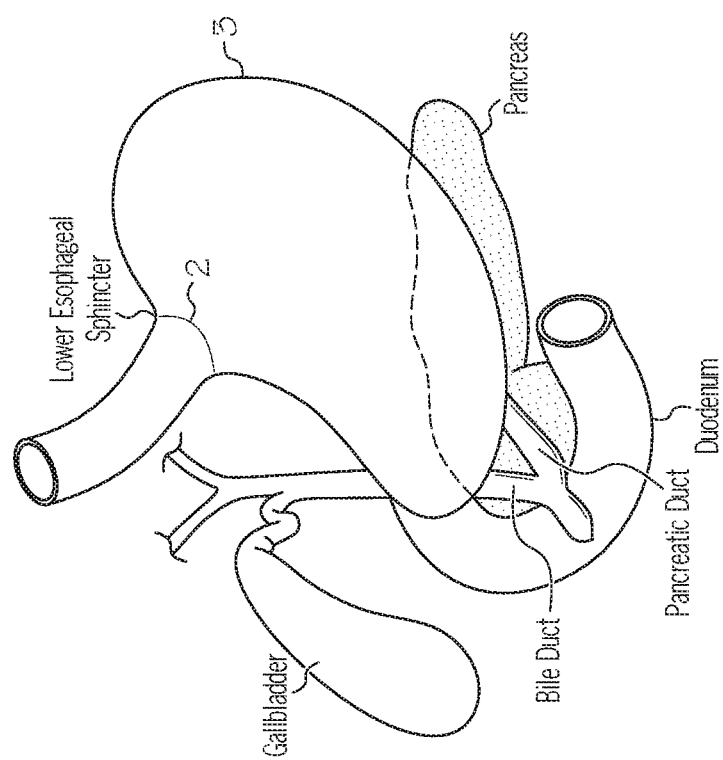
FIG. 3 is a schematic view of the geometry of the stomach prior to sleeve gastrectomy or biliopancreatic diversion with duodenal switch.
Figure 5:
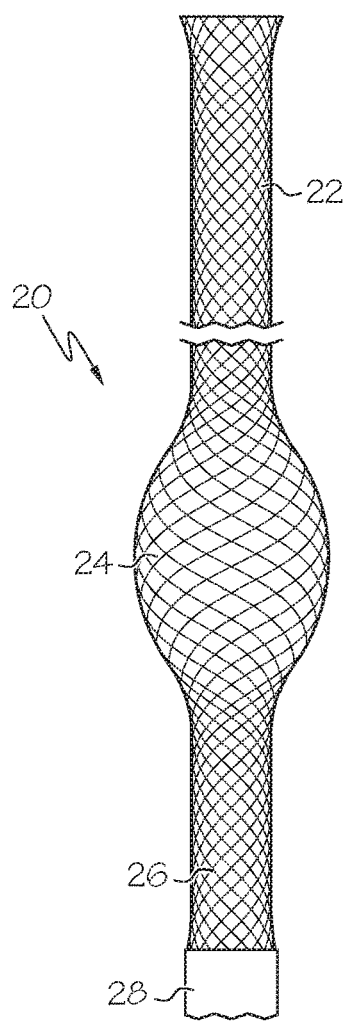
FIG. 5 is a partial view of one embodiment of a stent according to the disclosure for use after sleeve gastrectomy or biliopancreatic diversion with duodenal switch.

Turning now to the figures, FIG. 5 is a partial side view of one embodiment of a stent according to the disclosure. Stent 20 includes a flared proximal end portion 22, an enlarged middle portion 24 and a distal end portion 26 connected to a polymeric sleeve 28. Sleeve 28 is partially illustrated in FIG. 5.

While the enlarged middle portion 24 is shown in FIG. 5 as having a symmetrical ovular shape, the shape may also be non-symmetrical as well. This stent is designed to pass from the esophagus, through the stomach, and into the duodenum. Sleeve 28 extends distally past the distal end of the distal end portion 26 of the stent 20 and past the common bile duct.

Sleeve 28 is suitably formed of a material that allows it to collapse upon itself. This, in combination with the extension of the sleeve 28 beyond the common bile duct, allows the bile to fun down the outside of the sleeve and continue into the small intestine rather than splashing back into the stomach.

Sleeve 28 is suitably formed of a polymer material, and can also be formed of an elastomeric polymeric material.

Examples of polymers include Teflon, PTFE, FEP, polyethylene and polypropylene.

Examples of elastomeric polymers include, but are not limited to, silicone, polyurethane and polyether-block-amide to mention only a few.

Figure 6:
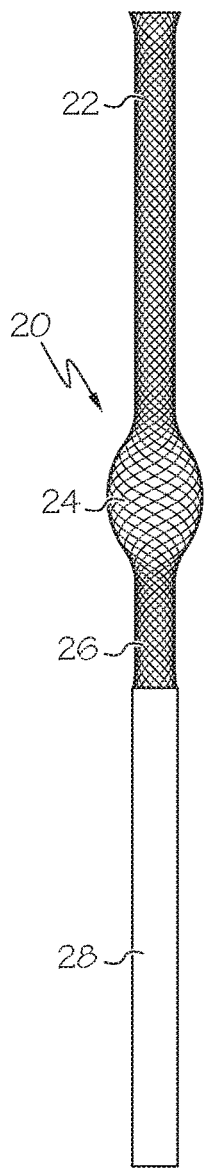
FIG. 6 illustrates a stent which is similar to the embodiment shown in FIG. 5.

FIG. 6 is a side view of a stent 20 similar to that shown in FIG. 5, with the relative length of sleeve 28 to stent 20.

Figure 7:
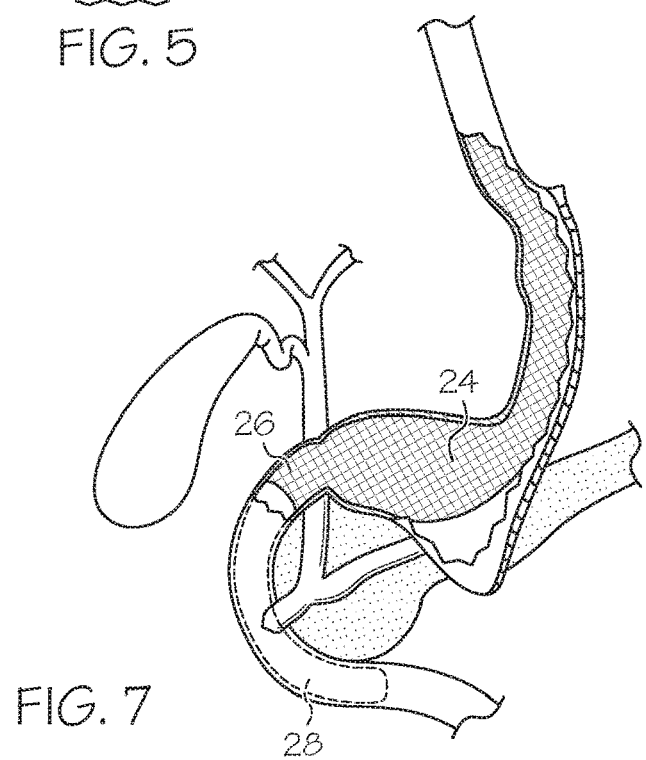
FIG. 7 is a schematic view illustrating a stent similar to that shown in FIG. 5 wherein the stent is shown extending through the stomach, the pylorus and into the duodenum.

FIG. 7 illustrates a stent 20 similar to those shown in FIGS. 5 and 6 wherein stent 20 is illustrated passing from the esophagus, through the stomach and into the duodenum. The sleeve 28 of stent 20 extends distally past the distal end or the distal end portion 26 past the common bile duct into the duodenum. Proximal end portion 22 of stent 20 is in the esophagus, the enlarged middle portion 24 is located in the antrum of stomach and distal end portion 26 along with sleeve 28 is located in the duodenum.

Figure 8:
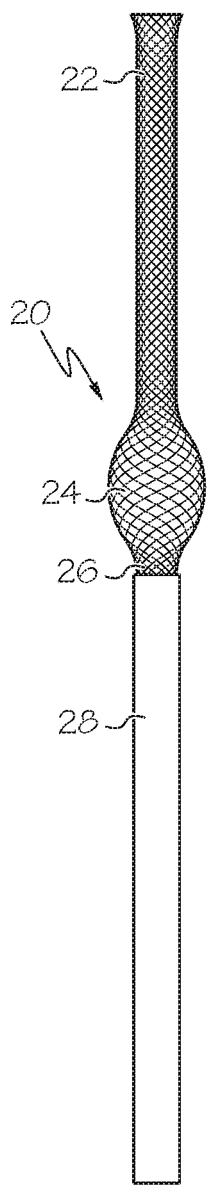
FIG. 8 illustrates another embodiment of a stent, according to the disclosure.

FIG. 8 is a side view of an alternative embodiment of a stent 20 wherein the distal end portion 26 of stent 20 is relatively short, or just slightly greater than 0 mm and ends almost at the distal end of the enlarged central portion 24 of stent 20. In this embodiment, the stent/sleeve is configured such that the sleeve 28 of the stent terminates in the stomach rather extending into the duodenum as illustrated in the embodiment shown in FIG. 7. Again, as in the embodiment shown in FIG. 7 above, sleeve 20 extends beyond the common bile duct.

Again, sleeve 20 is configured to collapse and close upon itself to prevent bile reflux. In this embodiment, however, the pyloric valve is still able to close to further aid in the prevention of bile reflux.

Figure 9:
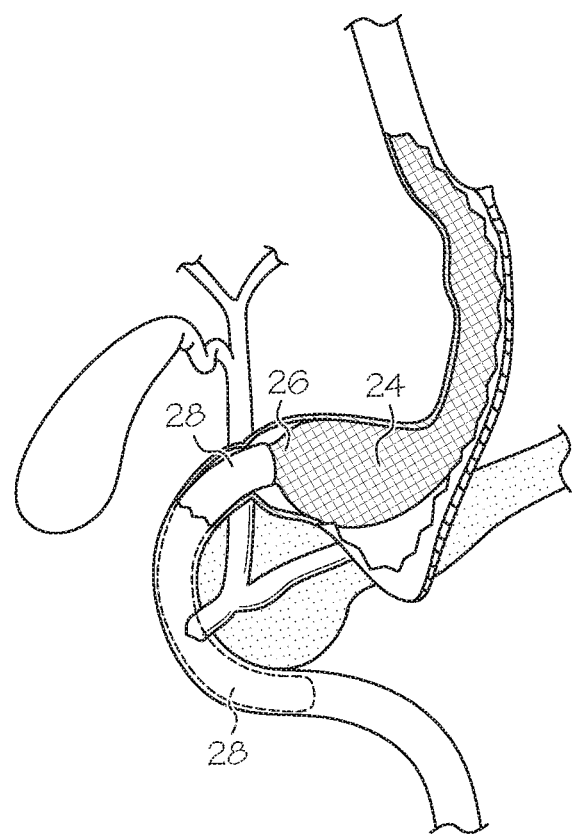
FIG. 9 is a schematic view illustrating a stent similar to that shown in FIG. 8 wherein the distal end of the stent stops in the stomach before the pylorus.

FIG. 9 illustrates stent similar to that shown in FIG. 8 wherein stent 20 is shown passing from the esophagus, through the stomach, and ending in the pylorus. The enlarged central portion and the distal end 26 thereof, thus terminates in the stomach. The sleeve 28 of stent 20 passes through the pylorus 16 of the stomach and into the duodenum 5. In this embodiment, only the sleeve 28 is located in the duodenum.

Figure 10:
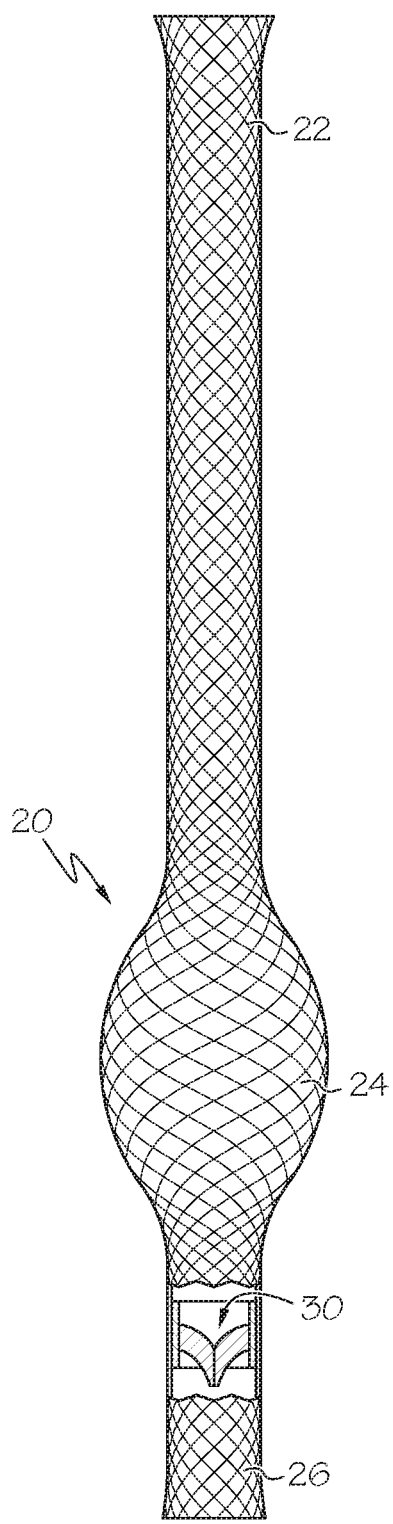
FIG. 10 illustrates another embodiment of a stent having a one way valve disposed therein.

FIG. 10 is a side view of an alternative embodiment of a stent 20 wherein the sleeve 28 is eliminated. In this embodiment a valve 30 is positioned in the distal end portion 26 of the stent between the enlarged central portion 24 and the distal end of stent 20.

In one embodiment, the stent includes a one-way flow valve.

In some embodiments, the one-way flow valve may comprise one cuspid or multiple cuspids.

Figure 11:
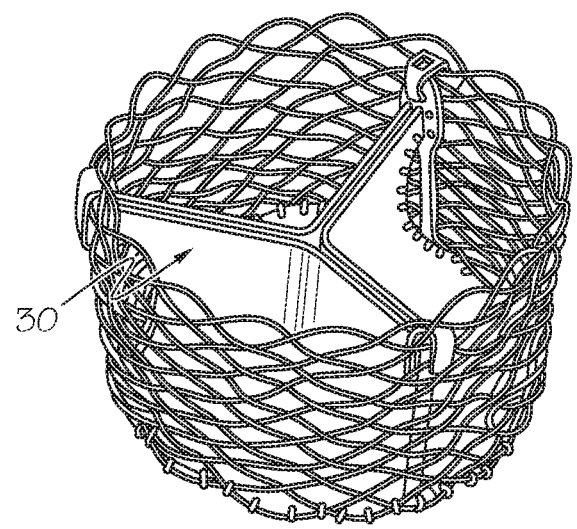
FIG. 11 illustrates one embodiment of a valve that may be used in accordance with the stent shown in FIG. 10.

In one embodiment, the stent includes a tricuspid one-way valve as shown in FIG. 11.

Positioning of a one way valve in the distal end portion 26 of stent 20 aids in the prevention or significant reduction of bile reflux. The valve 30 is positioned within the distal end portion 26 of stent so as to reside at approximately the same location as the pyloric sphincter.

In some embodiments, stent 20 is in the formed of a braided or woven structure. Valve 30 may be coupled to the braided or woven construction.

Figure 12:
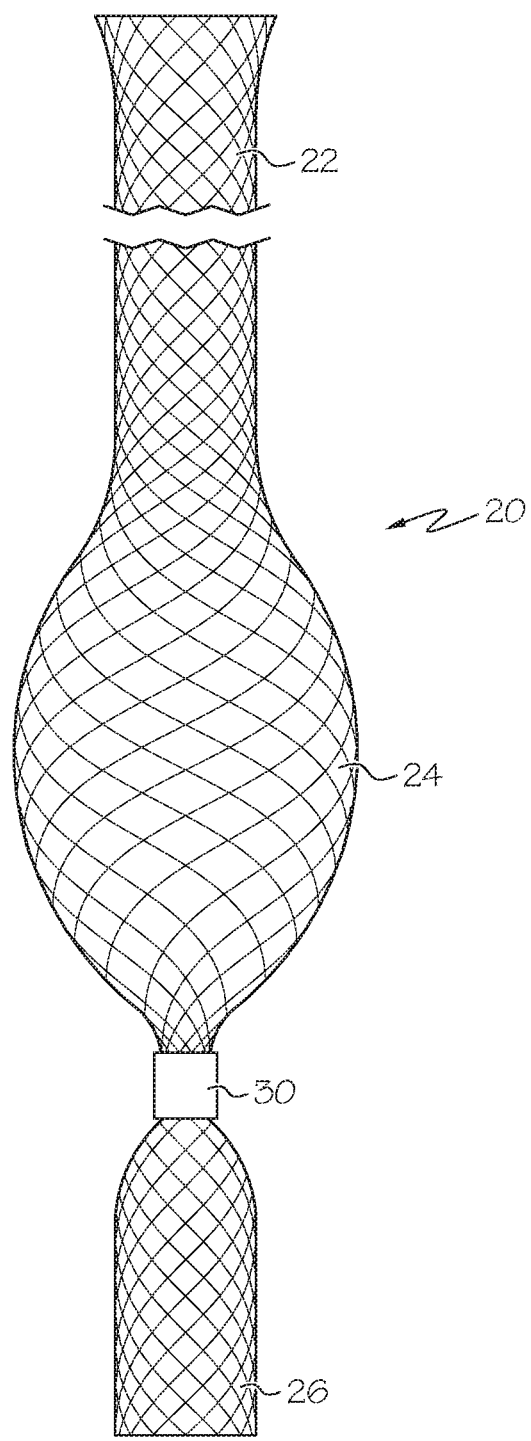
FIG. 12 illustrates an alternative embodiment of a stent, according to the disclosure.
Figure 13:
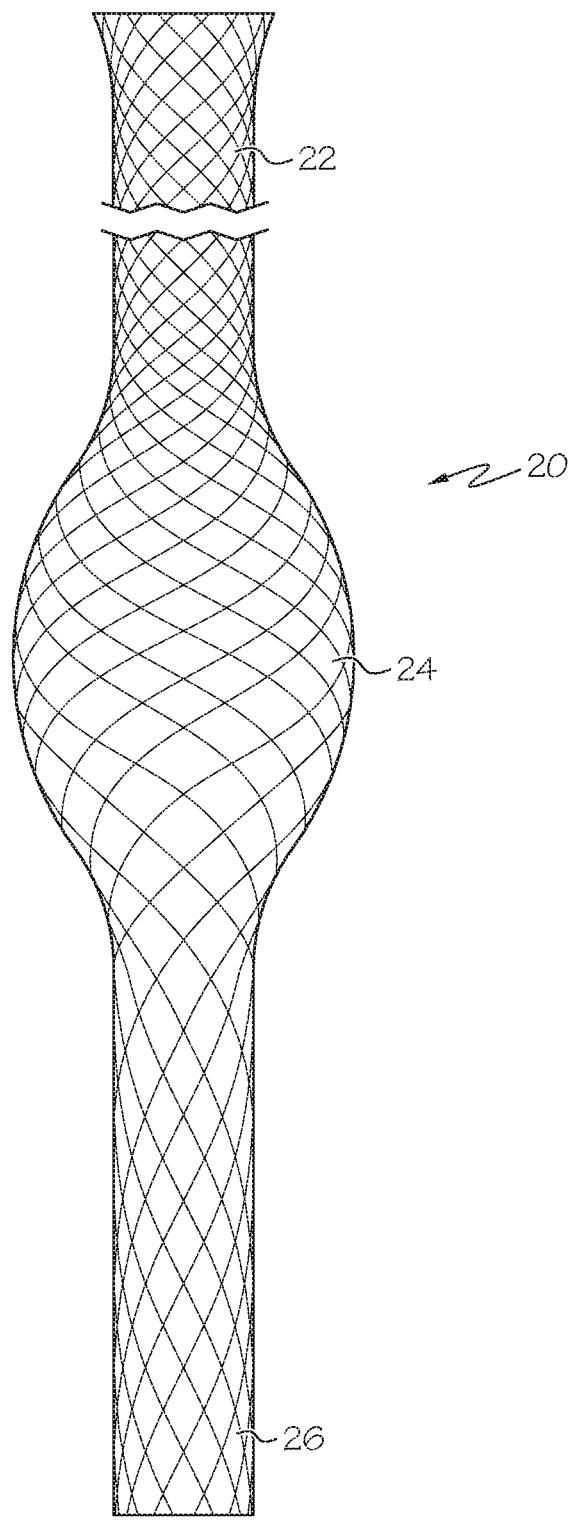
FIG. 13 illustrates another alternative embodiment of a stent, according to the disclosure.

FIGS. 12 and 13 illustrate alternative embodiments wherein at least a portion of the distal end portion 26 which will be disposed in the pyloric sphincter comprises a collapsible stent portion. The collapsible portion can be created in a variety of ways such as by reducing the radial strength of the stent in at least a portion of the end portion 26 or the entire portion, or by placing a collapsible sleeve or band around at least a portion of the distal end portion 26.

FIG. 12 is a side view illustrating an alternative embodiment of a stent 20 wherein the valve 30 has been replaced with an elastomeric band 32. Band 32 may be formed of any suitable elastomeric material. Examples include, but are not limited to, silicone, polyurethane and poly-ether-block amide.

Elastomeric band 32 is located in the distal end portion at the distal end of the enlarged middle portion 24 of stent 20.

Elastomeric band 32 applies an inward pressure such that stent 20 closes upon itself in the region of elastomeric band 32.

When the stomach muscles contract, the bolus of food will be pushed out of the stomach bulge, past the elastomeric band, and into the duodenum. This causes the elastomeric band to expand. Once the bolus of food has passed, the elastomeric band returns to it's at rest state wherein the stent 20 in the region of elastomeric band 32 is again closed, preventing or significantly reducing bile reflux.

The distal end portion 26 of stent 20 can be formed of a braided or woven construction as the rest of stent 20, but can be suitably formed of a continuous wall construction in this embodiment, as opposed to a braided or woven configuration.

FIG. 13 is an alternative embodiment wherein the distal end portion 26 of stent 20 extends through the pyloric sphincter. At this location, the radial force of stent 20 is lower than the enlarged middle portion 24 of stent 20 and the proximal end portion 22 of stent 20 to allow closure of the sphincter. The radial force can be reduced in a variety of different was such as reducing the wire diameter, lowering the braid angle, reducing the number of wires, etc. FIG. 13 illustrates a reduction in braid angle in the distal end portion 26 of stent 20. The radial force may also be reduced only on a segment of the distal end portion 26 of stent 20 such as that portion closest to the enlarged middle portion 24 of stent 20.

In any of the embodiments disclosed above, stent 20 may be formed from any suitable stent material. Examples include, but are not limited to, nickel-titanium alloy (nitinol), cobalt-chromium-nickel alloy (elgiloy), cobalt-chromium alloy, or stainless steel.

In any of the embodiments disclosed above, the entirety of the stent, or any portions thereof, may be formed of a braided or woven construction.

In any of the embodiments disclosed above, the stent, or any portions thereof, may be a laser cut stent.

In any of the embodiments disclosed above, the entirety of stent 20 may include any appropriate cover, or any portion or portions thereof. The covering may be formed of any suitable material. Examples include, but are not limited to, polyesters, polypropylenes, polyethylenes, polyurethanes, polynaphthalenes, polytetrafluoroethylenes, expanded polytetrafluoroethylene, silicone, copolymers thereof and mixtures or combinations thereof. In some implementations, the polymeric cover is silicone.

A description of some embodiments of a stent delivery catheter, stylet for use therein and methods of using the same is contained in one or more of the following statements:

The invention claimed is:

1. A method for implanting a stent in portions of a patient's esophagus, stomach, and duodenum after bariatric surgery, the method comprising:
   inserting a stent into the esophagus, stomach, and duodenum, the stent including a stent portion having a proximal end portion, a distal end portion, an enlarged middle portion located between the proximal end portion and the distal end portion, and a polymeric cover disposed over the stent portion and extending distally beyond the distal end portion forming a polymeric sleeve portion; and
   positioning the stent with the proximal end portion extending into a distal portion of the esophagus, the distal end portion positioned in the stomach, the enlarged middle portion within a central portion of the stomach, and the polymeric sleeve portion extending into the duodenum.

2. The method of claim 1, wherein the enlarged middle portion has an enlarged diameter relative to both the proximal end portion and the distal end portion.

3. The method of claim 1, wherein the distal end portion of the stent terminates in the stomach.

4. The method of claim 1, wherein only the polymeric sleeve portion extends into the duodenum.

5. The method of claim 1, wherein the stent portion is formed of stent material, wherein the polymeric sleeve portion is devoid of stent material.

6. The method of claim 1, wherein the polymeric sleeve portion is elastomeric.

7. The method of claim 1, wherein the polymeric sleeve portion comprises silicone.

8. The method of claim 1, wherein the stent portion is braided, woven or laser cut.

9. The method of claim 1, wherein the stent portion comprises nickel-titanium alloy, cobalt-chromium-nickel alloy, cobalt-chromium alloy, or stainless steel.

10. A method for implanting a stent in portions of a patient's esophagus, stomach, and duodenum after bariatric surgery, the method comprising:
    inserting a stent into the esophagus, stomach, and duodenum, the stent including a stent portion having a proximal end portion, a middle portion, a distal end portion, and a polymeric cover disposed over at least the distal end portion and extending distally beyond the distal end portion forming a polymeric sleeve portion, the middle portion having an enlarged diameter relative to both the proximal end portion and the distal end portion; and
    positioning the proximal end portion within the esophagus, the middle portion within the stomach, and the polymeric sleeve portion extending into the duodenum.

11. The method of claim 10, wherein only the polymeric sleeve portion extends across the patient's pyloric valve.

12. The method of claim 10, wherein the distal end portion extends into and resides within the duodenum.

13. The method of claim 12, wherein at least a portion of the distal end portion of the stent comprises reduced radial strength, wherein a portion of the distal end portion is positioned to extend across the patient's pyloric valve, wherein the portion of the distal end portion comprises reduced radial strength and is configured to allow the pyloric valve to open and close.

14. The method of claim 10, wherein the distal end portion of the stent terminates in the stomach.

15. The method of claim 10, wherein the polymeric sleeve portion is elastomeric.

16. The method of claim 10, wherein the polymeric sleeve portion comprises silicone.

17. The method of claim 10, wherein the stent portion is braided, woven or laser cut.

18. The method of claim 10, wherein the stent portion comprises nickel-titanium alloy, cobalt-chromium-nickel alloy, cobalt-chromium alloy, or stainless steel.

19. A method for implanting a stent in portions of a patient's esophagus, stomach, and duodenum after bariatric surgery, the method comprising:
    inserting a stent into the esophagus, stomach, and duodenum, the stent including a stent portion having a proximal end portion, a middle portion, a distal end portion, and a polymeric cover disposed over at least the distal end portion and extending distally beyond the distal end portion forming a polymeric sleeve portion; and
    positioning the proximal end portion within the esophagus, the middle portion within the stomach, and the polymeric sleeve portion extending into the duodenum;
    wherein the distal end portion extends into and resides within the duodenum; and wherein at least a portion of the distal end portion of the stent comprises reduced radial strength, wherein a portion of the distal end portion is positioned to extend across the patient's pyloric valve, wherein the portion of the distal end portion comprises reduced radial strength and is configured to allow the pyloric valve to open and close.

* * * * *